United States Patent [19]

Timpe et al.

[11] Patent Number: 4,622,976

[45] Date of Patent: Nov. 18, 1986

[54] METHOD AND APPARATUS FOR CONDUCTING XENON INHALATION STUDIES

[75] Inventors: Gerald M. Timpe; Terry W. Deville, both of Houston, Tex.

[73] Assignee: Enhancer R & D, Houston, Tex.

[21] Appl. No.: 723,456

[22] Filed: Apr. 15, 1985

[51] Int. Cl.⁴ .............................................. A61B 6/00
[52] U.S. Cl. ............................... 128/654; 128/203.14
[58] Field of Search .................. 128/654, 719, 205.17, 128/204.21, 204.22, 204.23, 204.28, 205.13, 205.14, 205.15, 203.14

[56] References Cited

U.S. PATENT DOCUMENTS

| | | | |
|---|---|---|---|
| 3,881,463 | 5/1975 | LeMon | 128/654 |
| 3,890,959 | 6/1975 | Youdin et al. | 128/654 |
| 4,150,670 | 4/1979 | Jewett et al. | 128/204.22 |
| 4,169,465 | 10/1979 | Walls et al. | 128/719 |
| 4,202,345 | 5/1980 | Farella et al. | 128/654 |

OTHER PUBLICATIONS

Ruben, "Anaesthesia System with Eliminated Spill Valve Adjustment and without Lung Rupture Risk", Acta Anaesth. Scand., 1984; 28: 310-314.

Gur et al, "Simultaneous Mass Spectrometry and Thermoconductivity Measurements of End-Tidal Xenon Concentrations: A Comparison", Med. Phys. 11(2), Mar./Apr. 1984, pp. 209-211.

Primary Examiner—Henry J. Recla
Attorney, Agent, or Firm—Norvell & Associates

[57] ABSTRACT

Inhalation methods and apparatus are provided for performing xenon-enhanced studies or tests. The present invention is useful during computed tomography studies to provide neurologists with accurate yet relatively inexpensive measurements of cerebral blood flow. The apparatus includes a variable volume xenon-/oxygen chamber for obtaining a closed-loop arrangement with the patient, thereby minimizing xenon gas usage during the study. According to the method of the invention, the volume of the xenon/oxygen chamber is reduced during a first phase of the study, while the patient's lung xenon concentration increases. The second phase is initiated when the variable chamber obtains a selected minimum value, after which exhalation returns to the chamber. During the second phase, oxygen and xenon are added to the closed loop system to maintain the desired concentrations, carbon dioxide is removed, and the chamber volume slowly increases. Apart from xenon inhalation studies, the method and apparatus have utility for a wide range of inhalation procedures, especially those involving relatively expensive inhalation gases.

29 Claims, 2 Drawing Figures

METHOD AND APPARATUS FOR CONDUCTING XENON INHALATION STUDIES

BACKGROUND OF THE INVENTION

The present invention relates to techniques for providing inhalation gases to patients during experimental, clinical, and analytical studies and, more particularly, to methods and apparatus for conducting relatively high concentration enhanced gas studies utilizing a closed loop system.

Since at least the 1950s, neurologists have recognized the significance of cerebral blood flow for evaluating brain functions, e.g., cerebral metabolic rates. Low-concentration radioactive xenon inhalation studies have long been utilized to provide analysis of matter flow within multiple cerebral and brain-stem regions. The inability to measure blood tissue coefficients, poor resolution due to tissue overlap, and contamination by extracranial blood flow have, however, reduced the acceptance of radioactive xenon inhalation techniques for cerebral blood flow mapping.

In the late 1970s, neurologists began to explore the possibility of using relatively high concentration non-radioactive xenon gas to measure cerebral blood flow. Stable xenon gas freely passes the blood/brain barrier, and the heavy gas (Atomic No. 54) attenuates X-rays. As rapid, sequential transmission computed tomography (CT) scanners with a high signal-to-noise ratio became available, interest in xenon-enhanced inhalation studies heightened. Xenon-enhanced inhalation CT studies are currently utilized or considered for a wide range of experimental, clinical, and analytical tests, including tests to differentiate coma from brain death, studies for patients suffering from dementias and multiple sclerosis, and studies for patients experiencing trauma, vascular spasms, and seizures.

The expense of the xenon gas for such studies has, however, minimized research regarding and employment of xenon-enhanced/CT techniques. No universally acceptable method for conducting xenon-enhanced/CT studies exists, and therefore any efforts to minimize xenon gas costs must be compatable With various techniques. In general, xenon concentrations in end-tidal gas are assumed to be proportional to xenon concentrations in arterial blood, and xenon end-tidal gas concentrations are therefore an input function in the determination of cerebral blood flow. One technique for determining end-tidal concentrations is to utilize the "subtraction method", which requires patient exposure to 100% oxygen in order to obtain substantially total denitrogenation prior to xenon inhalation. Other common techniques for directly measuring end-tidal xenon gas concentrations utilize a mass spectrometer or a thermal conductivity detector.

Further variations regarding the procedure for conducting xenon inhalation studies depend on the particular desires of the neurologists and needs of the patient. Neurologists desires may vary from a relatively low 28% xenon concentration to a relatively high 40% xenon concentration, although 35% xenon concentration is a commonly-recognized norm. Oxygen inhalation concentrations will obviously depend upon the particular needs of the patient, and may increase from the norm of 21% to 50% or more for patients requiring increased oxygen levels, or to 100% for the pre-xenon inhalation period required to obtain patient denitrogenation.

Xenon-enhanced inhalation periods for cerebral blood flow analysis studies typically vary from about 4 to 7 minutes and those skilled in the art recognize that the cost of the xenon gas inhaled during such studies is a factor detrimental to xenon/CT acceptance in the industry. Although cost estimates vary, it is generally presumed that the xenon cost to patients for a single study may be in the range of from $50 to $150. Moreover, continual variations in xenon/CT techniques and data analysis experiments must be widely performed on test animals, such as baboons, prior to widespread utilization and acceptance of this technology in the medical industry. Xenon usage is therefore a significant cost to both experimental and clinical xenon-enhanced inhalation studies. Further background regarding xenon-enhanced cerebral blood flow studies may be obtained from the following articles: "Mapping Local Blood Flow Of Human Brain By CT Scanning During Stable Xenon Inhalation", by Meyer et al, *STROKE*, Vol. 12, No. 4, pp. 426-436, July-August 1981; "Xenon and CT Provide Cerebral Blood Flow Measure", *DIAGNOSTIC IMAGING*, September 1984, pp. 13-14; "Simultaneous Mass Spectrometry and Thermoconductivity Measurements of End-Tidal Xenon Concentrations: A Comparison", by Gur et al, *MED PHYS*, Vol. 11, No. 2, March-April 1984, pp. 209-212; and "Mapping Cerebral Blood Flow By Xenon Enhanced Computed Tomography: Clinical Experience", by Yonas et al, *RADIOLOGY*, Vol. 152, No. 2, August 1984, pp. 435-442.

The prior art does not provide an acceptable technique for substantially reducing xenon costs for such tests, while simultaneously providing a technique compatible with the various CT procedures. The disadvantages of the prior art are overcome by the present invention, and improved methods and apparatus are hereinafter described for performing xenon-enhanced studies. The method and apparatus of the present invention may also be used to reduce the cost of various other gases utilized in inhalation-related procedures.

SUMMARY OF THE INVENTION

An inhalation system is provided, including a variable volume gas chamber, closed loop circuitry, and controlled gas input devices for maintaining the desired gas concentrations during the study. When utilized for computed tomography enhanced-xenon studies, accurate and relatively inexpensive cerebral blood flow measurements may be obtained.

The circuitry preferably includes a plurality of automatically actuatable valves which allow for a decrease in the volume of the gas chamber during a first time period. During this first time period, the concentration of the selected gas, e.g., xenon, in the patient's lungs increases. When the gas chamber volume reaches a predetermined minimum value, exhalation gases are returned to the gas chamber, and the process continues in a closed-loop system. Carbon dioxide is removed from the closed loop system and oxygen is added to maintain the desired oxygen level. The concentration of the selected enhanced gas in the system, such as xenon, may be monitored and, in response thereto, added to the closed loop system to maintain the enhanced gas concentration within selected limits during the test or procedure.

The method and apparatus of the present invention may be easily utilized with conventional equipment for studying room air breathing patients, increased oxygen breathing patients, or ventilator patients. Moreover, the apparatus may be utilized with any of the various CT measurement techniques, and the xenon gas concentration level may be easily altered to any desired value.

It is a feature of the present invention to provide enhanced-gas inhalation apparatus including closed loop gas circuitry for recirculating in a closed loop system at least a significant portion of the enhanced gas. It is a further feature of the invention to provide relatively compact and inexpensive inhalation apparatus for minimizing inhalation costs.

It is a further feature of the invention to provide improved methods for providing a patient a predetermined concentration of an enhanced gas in a closed loop system, wherein the concentration of the enhanced gas exhaled from the patient's lungs is substantially increased prior to initiating the closed-loop system.

These and other features and advantages of the present invention will become apparent from the following detailed description, wherein reference is made to the Figures in the accompanying drawings.

IN THE DRAWINGS

DETAILED DESCRIPTION OF THE INVENTION

The methods and apparatus of the present invention may be utilized to substantially reduce the cost of an enhanced gas during various inhalation studies or procedures. As used herein, the term "enhanced gas" is defined as an inhalation gas or gases other than oxygen, having a substantially increased concentration compared to air, and which are intentionally subjected to a patient for a controlled period of time. For example, enhanced gases may be inhaled by a patient in order to detect certain responses during a test period, or may be applied to a patient as an anesthetic.

The present invention has particular utility for reducing enhanced gas costs during neurological studies. Such studies may be performed on room air breathing patients, increased oxygen breathing patients, or ventilator patients, and the present invention is compatible with differing patients and neurological studies. In the embodiment described below, the enhanced gas is xenon, which may be utilized during computed tomography studies to determine cerebral blood flow.

Figure 1:
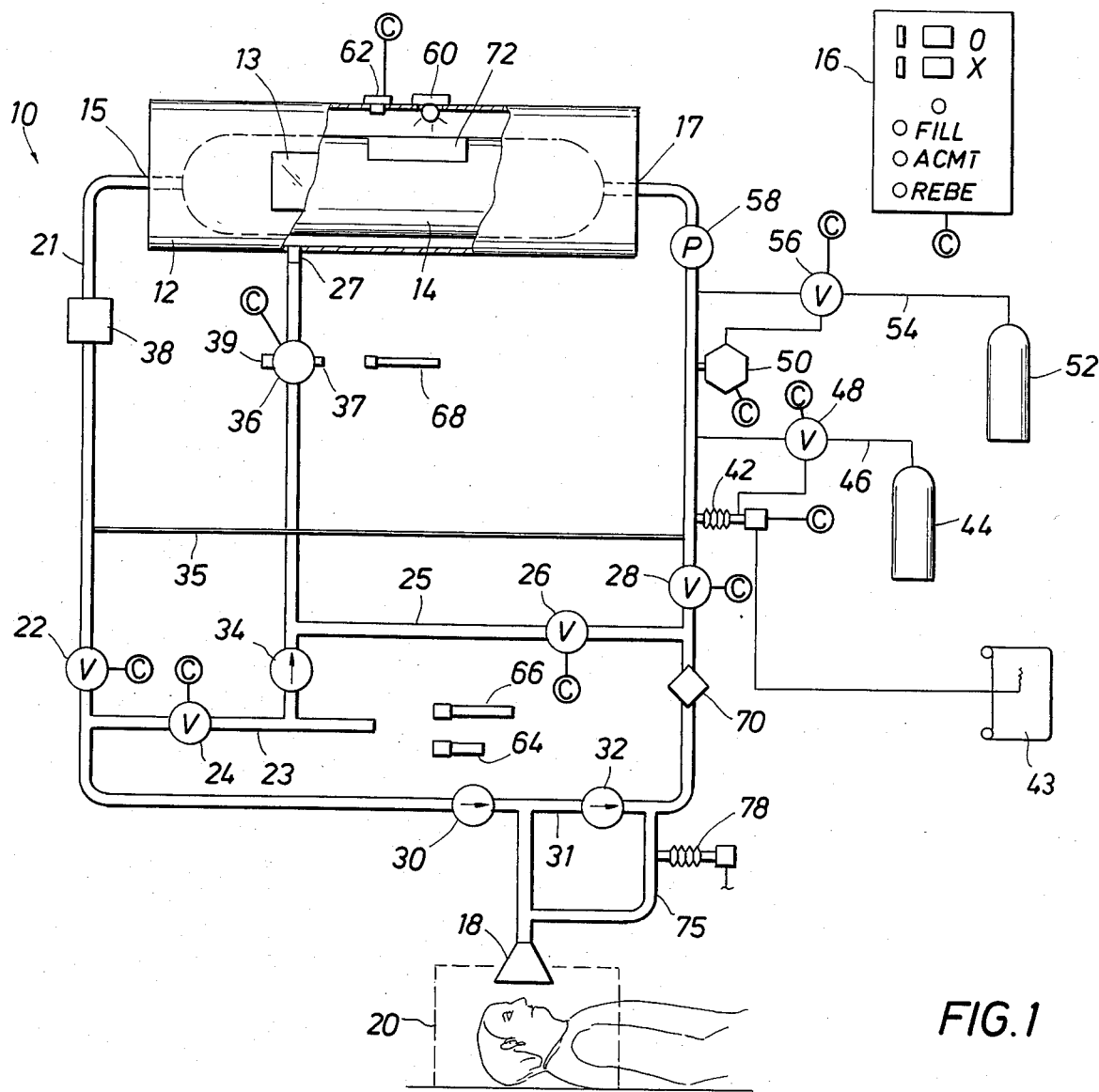
FIG. 1 is a schematic representation of a suitable xenon-enhanced inhalation system according to the present invention.

FIG. 1 is a schematic representation of an inhalation system according to the present invention. The device 10 consists of a rigid, generally cylindrical-shaped housing 12, a flexible housing 14 positioned within the rigid housing, a control panel 16, and inhalation face mask 18. Apparatus conforming to the schematic shown in FIG. 1 may be utilized for xenon-enhanced computed tomography studies, and the patient's head is illustrated positioned within a conventional CT scanner shown by dashed lines 20.

The rigid housing 12 may be conveniently fabricated from various plastic materials compatible with the gases to be used. If desired, a window portion 13 may be provided in the housing for viewing the flexible housing 14. Housing 14, also referred to as bag 14, may be fabricated from various repeatably expandable and contractable gas-tight materials compatible with the gases to be used, such as natural or synthetic rubber. The variable volume chamber within the bag 14 is connected in a closed-loop system with the mask 18 and therefore the patient's lungs. The patient inhales gas from bag 14 and, during at least a portion of the study, exhales gas to bag 14 in closed-loop fashion.

Conduit 21 connects the inhalation port 15 of the bag with mask 18, and conduit 31 completes the closed-loop by similarly connecting the mask 18 with the exhalation port 17 of the bag. A pair of check valves 30 and 32 are provided closely adjacent each side of the mask 18 to limit gas flow during both inhalation and exhalation in a single direction through the closed-loop. Normally-closed valves 22 in line 21 and 28 in line 31 may be controlled to allow or prohibit gas flow through the closed-loop, and will be subsequently discussed. Gas pump or blower 58 may be provided in the loop for assisting in circulating gas between the bag and mask, and for providing a homogeneous mixture of gases in the bag.

Room air/ventilator line 23 is open to atmosphere at port 40, and is connected at its other end to line 21. Normally-open valve 24 is provided for controlling gas flow through line 23. As explained subsequently, line 23 may be utilized to enable the patient to breathe room air, or to allow the patient to breathe an increased oxygen concentration by connecting port 40 to an oxygen source, or to add room air to the closed-loop system.

Line 25 interconnects line 31 to port 27 of housing 12. Gas may be discharged from the closed-loop by opening normally-open valve 26 in line 25 and allowing gas to be released through peep valve 36 in line 25. Also, pressurized gas from a ventilator may be input to housing 12 by closing valves 24 and 26 and passing gas through line 33 interconnecting lines 23 and 25. Check valve 34 in line 33 prohibits gas from passing from line 25 to line 23. Finally, a small diameter bypass line 35 interconnects lines 21 and 31 to enable recirculation of gas through a portion of the closed-loop system when valves 22 and 28 are closed. If desired, bypass line 35 may be left open when valves 22 and 28 are subsequently opened for an inhalation study, in which case line 35 forms part of the closed loop system. Apart from the patient's lung capacity, the closed loop volume is defined by bag 14, lines 21, 31, 35, 74 and 75.

Other components of the device 10 connected to the closed-loop system include a carbon dioxide absorber 38, a xenon concentration detector 42 and recorder 43, a pressurized xenon gas source 44 interconnected to line 31 via line 46 and control valve 48, an oxygen detector 50, and a pressurized oxygen gas source 52 interconnected to line 31 via line 54 and control valve 56. The xenon detector 42 is designed to measure xenon concentrations within the closed-loop system. In order to better measure xenon concentration in end-tidal gas, a thermal conductivity detector 78 may be included in line 75. Sample line 75 is in parallel with portion of lines 31 and 74, and allows exhalation gas from the patient to be sampled by the detector 78 for measuring and recording end-tidal xenon concentration. A carbon dioxide level detector 70 may also be provided in the system, and conveniently may be interconnected with sample line 75.

The procedure for utilizing the device 10 and the method of the present invention are described below for different classifications of patients.

Room Air Breathing Patients

Room air breathing patients are generally defined as patients which require neither increased oxygen concentrations nor breathing assistance. Before attaching the face mask or mouthpiece 18 to the patient, the deesired xenon and oxygen concentrations may be input to the closed loop system from respective digital potentiometers on control panel 16. The respective connections between control panel 16 and the various components of the device 10 are illustrated by an encircled "C". A FILL button on the control panel 16 may be activated to solenoid valves 48 and 56 and enable xenon and oxygen to be added to the system from sources 44 and 52, respectively. During the fill mode, solenoid valves 22 and 28 may be automatically and selectively opened or closed as explained below. Pump 58 Will circulate gas from bag 14 through port 15 and line 35, past the xenon detector 42 and the oxygen detector 50, and then through port 17 and back into bag 14. The xenon and oxygen concentrations in the system may be either measured or simply detected as being lower than or equal to the desired concentration. A signal indicative of the detected level may be compared to a signal indicative of the desired concentration, and a signal from the comparator used to control the opening or closing of the valves 48 and 56, respectively. Xenon and oxygen will therefore be added until the desired concentration for each gas is obtained in the system. For a typical room air breathing patient, the desired oxygen concentration would be 21%, and the desired xenon concentration may be 35%.

It is generally preferable prior to initiating xenon inhalation that the volume in the bag 14 reach a preferred initial gas volume. For a typical xenon study, this desired initial gas volume may be in the range of from 4 to 5 liters. The volume in the bag 14 may be conveniently determined by employing a light source 60 and a photocell 62 within the rigid housing 12. Most of bag 14 may be black, although a portion 72 may be painted white to better reflect light. The volume of the bag will govern the position of white portion 72 within the housing relative to the light source 60 and photocell 62, and therefore the amount of light received by photocell 62 may serve as an indication of bag volume. If the bag volume is not within its desired initial range and the oxygen and xenon concentrations are at their respective desired concentrations, solenoid valve 28 may be briefly opened to allow the addition of room air into the system. When room air is added to the system, the xenon concentration will decrease, and further xenon may be automatically added to the system by opening valve 48 until the desired xenon concentration is again obtained. The addition of xenon gas to the system will result in a decrease in the oxygen concentration, so that oxygen will then also be added to the system by opening valve 56 to maintain the desired oxygen concentration. If, on the other hand, the bag volume has reached its desired initial volume although the desired xenon and/or oxygen concentrations have not been obtained, gas may be discharged from the system by selectively opening valve 28, and discharging gas through line 25 and out peep valve 36 by reversing blower 58. With the reduced gas volume in the system, additional xenon gas may then be added, so that the desired oxygen and xenon concentrations are obtained with the bag volume within its preferred initial volume range.

It should be understood that by pressing the fill button, the system of the present invention may automatically fulfill the desired gas concentration and initial bag volume requirements. Conventional electronic circuitry (shown at 95 in FIG. 2) may therefore be included in device 10 for satisfying the input requirements for the system and activating the valves discussed herein. It is, however, also within the concept of the invention to manually open and close valves as described above in order to fulfill these initial objectives. Regardless of the procedure utilized, it may now be presumed that bag 14 will be within its desired initial volume range of from 4 to 5 liters, while the oxygen and xenon concentrations in the bag are at 21% and 35%, respectively. Once these conditions have been obtained, a signal indicative of each condition from photocell 62, xenon sampler 42 and oxygen sampler 50 will be received by the control circuitry, and a ready light on the control panel may be automatically activated to indicate that the system is ready for use.

It is generally desirable to have a patient become accustomed to the device prior to initiating xenon inhalation. Accordingly, after the ready light is on, the device may automatically switch to the acclimate mode, or this function may be normally controlled by depressing the ACMT button on the control panel 16. In the acclimate mode, valves 22 and 28 will be closed, and valves 24 and 26 open. The patient may then be attached to the face mask or mouthpiece 18, and will breathe room air through port 40 and line 23. The patient will exhale air through lines 74 (and 75), 31, and 25 and out peep valve 36. During the acclimate mode, the patient is not inhaling any xenon gas, but simply is becoming acclimated to the device.

Once it is desired to have the patient start breathing xenon gas (which generally coincides with the commencement of the CT study), the REBREATHE or REBE button on panel 16 may be activated, which will initiate the first stage of the two-phase inhalation process. During phase 1, valve 24 is automatically closed, and valve 22 is open (valve 25 is already closed, and valve 26 is already open). The patient therefore inhales gas from bag 14 via line 21, and exhales gas through lines 25 and 31 and out peep valve 36. During this first phase, the patient's xenon concentration in the lungs is increasing, and the volume of gas in bag 14 is decreasing.

When the volume in bag 14 reaches a selected minimal value, phase 2 is automatically activated. The determination of reaching this minimum volume may be automatically obtained through light source 60 and photocell 62, as explained above. According to the present invention, this minimum volume for xenon-enhanced CT inhalations will generally be in the range of from 0.5 liters to 1.5 liters. At the conclusion of phase 1, the exhaled xenon concentration will have increased to approximately 15% to 25%. Approximately 1% or less of the 35% inhaled xenon is absorbed in the patient's blood stream during the test, and stage 1 is utilized to substantially increase the xenon concentration in the dead space between valves 22 and 28 (inclusive of the patient's lungs) without diluting the closed loop systems. At the termination of phase 1, phase 2 is simultaneously initiated and valve 28 is opened while valve 26 is closed. The patient is therefore inhaling gas having the desired xenon concentration from bag 14 via line 21, and is exhaling gas back into bag 14 via line 31. During phase 2, the open port of peep valve 36 allows air to flow into and out of the housing 12, so that the bag 14 can expand and contract With the patient's breathing.

Once phase 2 is commenced, the xenon concentration in the system will be initially diluted since xenon concentration of exhaled gas is less than 35%. Additional xenon gas will therefore automatically be added to the system by opening valve 48, and with the addition of xenon gas to the system, additional oxygen will be added through valve 56 to maintain the desired conentration. After the patient has been breathing for several minutes during phase 2, the patient will exhale approximately 35% xenon, and no more xenon will have to be added to the system. During the time period between the initiation of phase 2 and this final equilibrium condition, the volume of bag 14 will be increased by the addition of xenon and oxygen gas to the system.

During phase 2, oxygen will obviously have to be continually added to the system and carbon dioxide removed from the system to compensate for the normal metabolic processes of the patient. Carbon dioxide may be readily removed by carbon dioxide absorber 38, and oxygen may be added by opening valve 56 in response to the detected concentration of oxygen in the system from 50. The volume of carbon dioxide that is removed from the system is substantially equal to the volume of oxygen that is added, and no increase in volume occurs during phase 2 due to the metabolic process. During the entirety of the test, the carbon dioxide level of the exhalation gas may be monitored and recorded with detector 70.

Upon conclusion of the study, the device may be switched back to the ACCLIMATE mode by pressing the ACMT button, and the face mask 18 may be removed from the patient. Some volume of gas will generally remain within bag 14 at the conclusion of the study, and this gas volume and concentration may be adjusted as previously explained prior to initiation of another test. If necessary, valve 22 may be opened and the system flushed while new gas having a desired oxygen concentration is added to the system for the next test.

Increased Oxygen Breathing patients

Enhanced xenon studies are frequently performed on patients receiving increased oxygen concentrations from conventional oxygen administration systems. Initially, the higher desired oxygen concentration may be input to the system as previously explained, and once these concentrations and the desired bag volume are obtained, the ready light will become activated and the unit may automatically switch to the ACCLIMATE mode. For the present, we will assume that an oxygen concentration of 40% has been selected, while a xenon concentration of 30% has been selected.

The patient's head may be positioned within the CT scanner 20 while the patient continues to breath from the portable oxygen administration system. With the device 10 in the acclimate mode, valves 22 and 28 will be closed and valves 24 and 26 open. The oxygen source tube 64 from the portable oxygen system may then be removed from the patient, and the mask 18 applied to the patient while simultaneously placing oxygen source tube 64 over port 40. During this acclimate mode, the patient will therefore continue under same breathing conditions as if connected to the increased oxygen administration system.

Once the patient has become acclimated to the device, the REBE button on control panel 16 may be activated, and the unit will perform in a manner similar to that described above, except that 40% oxygen and 30% xenon will be continually provided to the patient. During the test, the unit will operate in both phase 1 and phase 2, as previously explained.

Respirator Patients

Respirator patients require at least partial breathing assistance, and the apparatus of the present invention may be easily utilized in conjunction with a conventional ventilator. Since ventilator patients are generally receiving increased oxygen, it may be assumed that the unit has been initially filled to the desired concentration, for example, of 50% oxygen and 35% xenon in a manner as previously described.

Once the device 10 has been placed in the acclimate mode, the ventilator mask (not shown) may be removed from the patient and mask 18 placed on the patient while the ventilator inhalation tube 66 is removed from the ventilator mask line and attached to port 40 of line 23. Also, the ventilator exhalation valve tube 68 may be detached from the ventilator exhalation valve and attached to port 37 of peep valve 36. During the acclimate mode, the ventilator forces 50% oxygen concentration gas during inhalation through tube 66 and line 23 and into the patient, while simultaneously closing the exhaust port 39 of peep valve 36 and pressurizing the interior of the housing 12. Since the valves 22 and 28 are closed, pressurizing housing 12 has no effect. During exhalation, the exhaust port 39 of peep valve 36 opens, and the air is released from both the patient's lungs and housing 12.

During phase 1 of the test mode, valves 24 and 28 are closed and valves 22 and 26 are opened. During ventilator inhalation, pressure from the ventilator is passed through tube 66 and line 33 and applied to the housing 12, compressing the bag 14 and forcing gas from the bag to the patient. During inhalation, pressure from exhalation valve tube 68 closes the release port of peep valve 36. During ventilator exhalation, the absence of pressure in tubes 66 and 68 automatically opens peep valve 36, and the xenon-enhanced gas inhaled from bag 14 is exhaled out peep valve 36. The volume of the bag 14 is thus reduced in the manner previously described.

During phase 2 of the rebreathe mode, valve 26 is automatically closed and valve 28 is opened. During ventilator inhalation, pressure from tube 66 continues to expel gas from bag 14 to the patient as described above. During ventilator exhalation, however, xenon gas is returned to the breathing bag in the desired closed-loop fashion. During exhalation, the peep valve automatically opens, thereby allowing gas to be expelled from the interior of housing 12 so that bag 14 may be filled with exhalation gas.

A preferred range for the bag volume upon initiating a xenon-enhanced CT study for cerebral blood flow analysis is 4 to 5 liters, and a preferred bag volume range for initiating phase 2 of the test is between $\frac{1}{2}$ to $1\frac{1}{2}$ liters. In general, it is within the concept of the present invention to substantially reduce the bag volume from its maximum value to as low a volume as practical consistent with safety standards before commencing the closed loop phase of the ventilation operation. As previously explained, a light and photocell may be used to determine bag volume during any phase of the procedure. Other means of determining bag volume are, however, within the scope of the present invention, and include strain gauges positioned on the bag exterior to measure expansion of the bag material, low pressure sensors responsive to the pressure differential between the interior of the bag and the interior of housing 12, a bag exterior position sensor and transducer for sensing the position of a signaling member on the bag, or an acoustic generator and monitor positioned within the housing 12 and responsive to the volume differential between chambers 12 and 14. Also, it should be understood that initiation of phase 2 is preferably responsive to a signal directly indicative of a selected minimum bag volume, although the minimum bag volume may be indirectly measured by knowing the bag volume upon initiating phase 1 and the approximate breathing rate and lung capacity of the patient, and measuring the time since the initiation of phase 1 to approximate the desired bag volume for initiating phase 2.

The selected maximum bag volume is a function of both the desired gas volume when initiating phase 1 preferably high to substantially increase the exhalation enhanced gas concentration as the bag volume decreases (prior to initiating phase 2), and the bag volume upon initiating phase 2 plus the volume of enhanced gas added to the closed loop system after the commencement of phase 2 (to maintain the desired gas concentration during the test). For a majority of ventilation studies, the enhanced gas exhalation concentration preferably rises to a range of approximately 50% to 80% of its desired inhalation concentration before commencing phase 2. For the enhanced xenon study described herein, this range is obtained after patient inhalation of approximately 2 or 3 liters of gas, so that a signal indicative of 1 liter remaining in the bag 14 will trigger phase 2. After the bag volume has been reduced to this desired low value and phase 2 begins, xenon may be added to the system to maintain the desired inhalation concentration, and the bag volume will slowly increase but will be maintained at or below the 4 to 5 liter maximum bag capacity.

It should be understood that after initiation of phase 2, the exhalation gas concentration will continue to rise, e.g., from 25% to 35%, during a period of perhaps 2 to 4 minutes. Once the exhalation enhanced gas concentration reaches the desired inhalation enhanced gas concentration, no further enhanced gas need be added to the closed loop system. This system equilibrium condition (no change in closed loop volume, and the addition of oxygen and removal of carbon dioxide) may occur prior to the commencement of the inhalation test. It may therefore be understood that the maximum bag volume may be independent of the duration of the enhanced gas test. If the enhanced gas is an anesthetic gas, for instance, the maximum bag volume may be relatively small, i.e., under 10 liters, although the period for administering gas may be 1 hour or more.

The apparatus and methods of the present invention are particularly suitable for inhalation procedures utilizing a relatively expensive enhanced gas. Since enhanced gas is "saved" during the closed loop phase 2 of the test, the cost of the enhanced gas has a direct bearing on the practical applications of this system to various inhalation procedures. According to the present invention, the concentration of the inhaled enhanced gas, is relatively high, i.e., in excess of 5% by volume and preferably in excess of 10% by volume, so that the substantial increase in the enhanced gas exhalation concentration prior to initiation of phase 2 is utilized to enable the use of a relatively small maximum volume variable chamber.

With a variable volume apparatus having a selected maximum volume chamber or bag 14, the maximum concentration for the enhanced gas obtainable during both the FILL and REBE modes will be inversely proportional to gas volume upon initiating that mode. This maximum enhanced gas concentration will also be directly proportional to the enhanced gas concentration when first initiating the mode, and inversely proportional to the desired oxygen concentration for the patient less the oxygen concentration when initiating the mode. Accordingly, it should be understood that an increase in the desired oxygen concentration for the patient from 21% may limit the maximum desired enhanced gas concentration obtainable with a given apparatus. Also, the higher the enhanced gas concentration at the end of phase 1, the higher the maximum enhanced gas concentration may be for a given system. Within a system, the maximum desired oxygen concentration and the maximum enhanced gas concentration are thus related, and the present invention has particular utility when the combined desired enhanced gas and oxygen concentration is greater than 40% by volume.

It is a feature of the present invention to maintain a closed loop system (with the addition of oxygen and enhanced gas and the removal of carbon dioxide) during the entirety of the test period. This may be accomplished with a relatively small maximum bag volume, because (a) the bag volume has been substantially decreased during phase 1 of the test, and (2) the exhalation enhanced gas concentration has been substantially increased prior to initiating the closed loop system. If, however, the photocell were to indicate that the maximum bag volume was reached or were to be exceeded prior to the conclusion of the test, it is within the concept of the present invention to revert to phase 1 and thereby open valves 26 and 28 to allow for the escape of gas from peep valve 36. Gas volume in the closed loop system and the bag could thus be reduced, for example, from 5 liters to 4 liters, and then phase 2 returned and the closed loop process continued without interrupting the test. Also, if the bag volume were to decrease below a desired minimal value, e.g., 1.0 liters, during phase 2, valve 26 may be temporarily opened so that pump 58 would add room air to the system.

Figure 2:
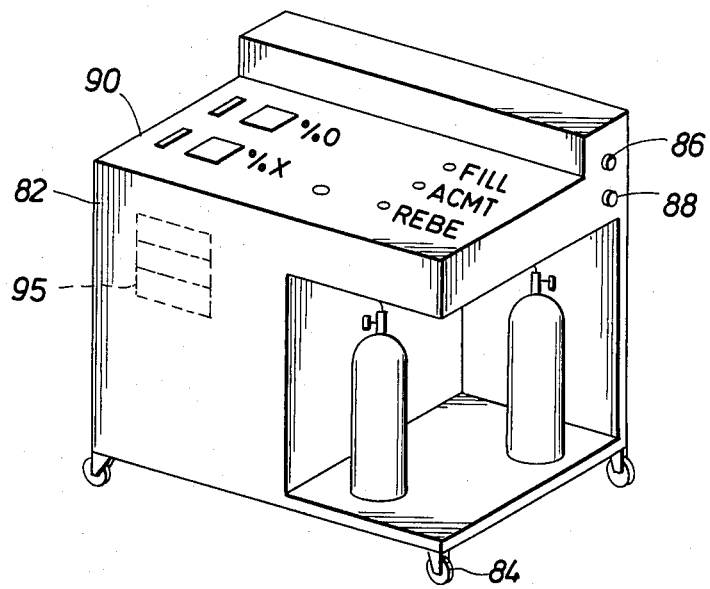
FIG. 2 is a pictorial representation of a suitable portable inhalation apparatus according to the present invention.

FIG. 2 illustrates a suitable embodiment of the apparatus according to the present invention. A portable cabinet 82 is provided on casters 84, and houses oxygen and xenon tanks. For simplicity, the gas circuitry is not illustrated in FIG. 2, although a number of connections 86 and 88 may be provided for attaching suitable hoses to form the closed loop circuitry discussed earlier. Control panel 90 is shown to illustrate typical controls discussed above, and a circuit board 95 is provided in the housing 12 for accomplishing the various signal comparison, bag volume determinations, and valve actuation operations discussed herein. The flow rate of blower 58 is preferably greater than the patient breathing rate, and may be in the range of from 20 to 30 liters of gas per minute. It is to be understood that commercially available carbon dioxide, xenon, and oxygen detectors, carbon dioxide absorber, gas pump, solenoid-actuated control valves, and peep valve may be used according to the present invention. Exemplary components are listed below:

| | | |
|---|---|---|
| 14 | Dupaco, #22905, Breathing Bag - 5 liters | |
| 24, 26 | Asco, #8030B-83, Normally Open Solenoid Valve - ⅜" | |
| 22, 28 | Asco, #8030B-3, Normally Closed Solenoid Valve - ⅜" | |

| | -continued | |
|---|---|---|
| 30, 32, 34 | Instrumentation Industries, #BE-130, One-Way Valve | |
| 36 | Instrumentation Industries, #BE-115, Exhalation Valve | |
| 38 | Commercial Filters, Fulflo, #WS-12/RW 55 Filter Jar with Grace Sodasorb (Soda Lime USP) | |
| 42, 78 | Gow-Mac Instru. Co., #10-133 TC Detector, Thermal Conductivity Cell | |
| 48, 56 | Asco, #U8262C2, Normally Closed Solenoid Valve - ¼" | |
| 50 | Teledyne Probe, #B10307B, with 0-2 Micro Fuel Cell #C6689, Class B-1 | |
| 62 | VACTEC, VT 501H Photocell | |

The term "patient" as used herein is intended to mean any person or animal that may be subjected to enhanced gas inhalation procedures. The term "ventilator" as used herein is intended to refer to any ventilator or inhalation device commonly utilized to assist patient breathing. The term "bag" as used herein is intended to refer to any expandable and contractable gas chamber. The term "mask" or "breathing mask" is intended to refer to any type of mask or mouthpiece for transmitting inhalation gas to a patient in a substantially sealed manner. The term "study" as used herein is intended to refer to any test or procedure utilizing enhanced-gas inhalation procedures. The term "enhanced gas" as used herein was earlier defined as an inhalation gas other than oxygen having a substantially increased concentration compared to air, and should be understood to include one or more desired gases for subjecting to a patient during a study.

The location of various components within the closed loop system, such as the gas pump or the carbon dioxide absorber, is not critical to the concept of the present invention. Also, the preferred inhalation gas circuitry will depend on the particular increased oxygen and ventilator apparatus to be utilized with the device according to the present invention.

It should be understood that various other modifications and changes may be made to the methods and apparatus described herein without departing from the spirit and scope of the present invention. Accordingly, embodiments disclosed herein and shown in the accompanying drawings should be understood as exemplary of the present invention, and not as limitations thereto.

What is claimed is:

1. Apparatus for conducting xenon-enhanced inhalation of a patient's lungs during neurological studies, including an oxygen source, a xenon source, and a patient breathing mask for transmitting inhalation gas to said patient, the improvement comprising:

a flexible bag defining a variable volume chamber for receiving said inhalation gas, said bag having an inhalation port and an exhalation port;

conduit means interconnected to said inhalation port, said patient breathing mask, and said exhalation port for series connecting said variable volume chamber and said patient's lungs in a closed loop;

a gas discharge port in fluid communication with said conduit means for releasing gas from said closed loop;

oxygen sampling means in fluid communication with said conduit means for detecting oxygen concentration within said closed loop;

xenon sampling means in fluid communication with said conduit means for detecting xenon concentration within said closed loop;

control means for providing preselected oxygen and xenon concentration values;

oxygen input valve means in fluid communication with said conduit means for selectively inputting oxygen from said oxygen source to said closed loop in response to a detected oxygen concentration value from said oxygen sampling means less than said preselected oxygen concentration value from said control means;

xenon input valve means in fluid communication with said conduit means for selectively inputting xenon from said xenon source to said closed loop to response to a detected xenon concentration value from said xenon sampling means less than said preselected xenon concentration value from said control means;

carbon dioxide removal means in fluid communication with said conduit means for removing carbon dioxide from said inhalation gas within said closed loop;

volume indicator means for detecting when said variable volume chamber obtains a predetermined minimum volume; and first valve means responsive to said volume indicator means for closing said gas discharge port and terminating gas discharge from said closed loop when said variable volume chamber obtains said predetermined minimum value;

wherein substantially all xenon gas is thereafter repeatedly exhaled from said patient's lungs to said flexible bag and retained within said closed loop.

2. The apparatus as defined in claim 1, further comprising:

a rigid housing defining a substantially fixed volume chamber for receiving said flexible bag, said rigid housing having an inlet port; and a gas pressure line for inputting pressurized gas through said inlet port and into said rigid housing for compressing said flexible bag and expelling said inhalation gas from said flexible bag to said patient's lungs.

3. The apparatus as defined in claim 2, further comprising:

an air sample/ventilation line for introducing gas having a desired oxygen concentration into said closed loop;

pump means for circulating said inhalation gas within said closed loop; and second valve means responsive to said volume indicator means for automatically opening to initiate fluid communication between said flexible bag and said patient's lungs when said variable volume chamber obtains a selected value.

4. The apparatus as defined in claim 1, wherein said volume indicator means comprises:

a light source for illuminating said flexible bag; and a light detector for producing a signal indicative of said flexible bag obtaining said predetermined minimum volume.

5. The apparatus as defined in claim 3, further comprising:

a line interconnecting said air sample/ventilator line to said inlet port of said rigid housing for inputting gas from said air sample/ventilator line into said rigid housing and expelling said inhalation gas from said flexible bag to said patient's lungs.

6. The apparatus as defined in claim 1, further comprising:

an end-tidal xenon sampler in fluid communication with said conduit means for measuring xenon concentration of gas exhaled from said patient's lungs.

7. The apparatus as defined in claim 1, wherein said flexible housing has a maximum volume in the range of from 4 liters to 5 liters.

8. The method of conducting enhanced gas inhalation of a patient, comprising:

inputting an initial volume of gas having a desired enhanced-gas concentration to a mixture of oxygen with a variable volume chamber;

forming a closed loop between said variable volume chamber and said patient;

detecting oxygen concentration in said closed loop;

detecting enhanced gas concentration in said closed loop;

inputting oxygen to said closed loop in response to said detected oxygen concentration to maintain a desired oxygen concentration;

inputting enhanced gas to said closed loop in response to said detected enhanced gas concentration to maintain a desired enhanced gas concentration;

removing carbon dioxide from said gas within said closed loop;

discharging said gas having said desired enhanced-gas concentration from said variable volume chamber to said patient;

releasing exhalation gas from said closed loop while reducing the volume of said variable volume chabmer during a first time period sufficient to substantially increase the enhanced gas concentration of said exhalation gas;

generating a first signal indicative of said variable chamber obtaining a selected minimum volume; and thereafter terminating release of said exhalation gas from said closed loop in response to said first signal and recirculating gas within said closed loop while adding enhanced gas to said closed loop in response to said detected enhanced gas concentration and increasing the volume of said variable volume chamber.

9. The method as defined in claim 8, wherein said selected minimum volume of said inhalation gas is between 0.5 and 1.5 liters.

10. The method as defined in claim 8, further comprising:

generating a second signal indicative of said variable chamber obtaining said initial volume of a selected value; and initiating discharge of said gas from said variable volume chamber to said patient in response to said second signal.

11. The method as defined in claim 10, wherein the combination of said desired oxygen concentration and said desired enhanced gas concentration is greater than 40% by volume.

12. The method as defined in claim 10, wherein said selected initial volume is less than approximately 5 liters.

13. The method as defined in claim 8, further comprising:

forming a rigid housing having a gas inlet for enclosing said variable volume chamber; and pressurizing said rigid housing for expelling said inhalation gas from said variable volume chamber to said patient.

14. The method as defined in claim 8, wherein said enhanced gas in said closed loop is maintained at a concentration of greater than 10% by volume.

15. Apparatus for conducting enhanced gas inhalation of a patient, comprising:

an oxygen source;

an enhanced gas source;

a flexible bag defining a variable volume chamber for receiving said inhalation gas;

conduit means for series interconnecting said variable volume chamber and said patient in a closed loop;

a gas discharge port in fluid communication with said conduit means for releasing gas from said closed loop;

oxygen sampling means in fluid communication with said conduit means for detecting oxygen concentration within said closed loop;

enhanced gas sampling means in fluid communication with said conduit means for detecting enhanced gas concentration within said closed loop;

control means for providing preselected oxygen and enhanced gas concentration values;

oxygen input valve means in fluid communication with said conduit means for selectively inputting oxygen from said oxygen source to said closed loop in response to a detected oxygen concentration value from said oxygen sampling means less than said preselected oxygen concentration value from said control means;

enhanced gas input valve means in fluid communication with said conduit means for selectively inputting enhanced gas from said enhanced gas source to said closed loop in response to a detected enhanced gas concentration value from said enhanced gas sampling means less than said preselected enhanced gas concentration value from said control means;

carbon dioxide removal means in fluid communication with said conduit means for removing carbon dioxide from said closed loop;

volume indicator means for detecting when said variable volume chamber obtains a predetermined minimum volume; and first valve means responsive to said volume indicator means for closing said gas discharge port and terminating gas discharge from said closed loop when said variable valve chamber obtains said predetermined minimum value.

16. The apparatus as defined in claim 15, further comprising:

a rigid housing defining a substantially fixed volume chamber for receiving said flexible bag; and a gas pressure line for inputting pressurized gas to said rigid housing for compressing said flexible bag and expelling inhalation gas from said flexible bag to said patient.

17. The apparatus as defined in claim 16, further comprising:

an air sample/ventilator line for introducing gas having a desired oxygen concentration into said closed loop;

pump means for circulating said inhalation gas within said closed loop; and second valve means responsive to said volume indicator means for automatically opening to initiate fluid communication between said flexible bag and said patient when said variable volume chamber obtains a selected volume.

18. The apparatus as defined in claim 17, further comprising:
a line interconnecting said air sample/ventilator line to said inlet port of said rigid housing for inputting gas from said air sample/ventilator line into said rigid housing and expelling said inhalation gas from said flexible bag to said patient's lungs.

19. The apparatus as defined in claim 15, wherein said indicator means comprises:
a light source for illuminating said flexible bag; and
a light detector for producing a signal indicative of said flexible bag obtaining said predetermined minimum volume.

20. The apparatus as defined in claim 19 wherein said predetermined minimum volume is from 0.5 to 1.5 liters.

21. The method of conducting enhanced gas inhalation of a patient, comprising:
inputting an initial volume of gas having a mixture of oxygen with a desired enhanced-gas concentration to a variable volume chamber;
forming a closed loop between said variable volume chamber and said patient;
detecting oxygen concentration in said closed loop;
detecting enhanced gas concentration in said closed loop;
inputting oxygen to said closed loop in response to said detected oxygen concentration to maintain a desired oxygen concentration;
inputting enhanced gas to said closed loop in response to said detected enhanced gas concentration to maintain a desired enhanced gas concentration;
removing carbon dioxide from said gas within said closed loop;
generating an initial volume signal indicative of said variable volume chamber obtaining said initial volume of a selected value;
initiating discharge of said gas having said enhanced-gas concentration from said variable volume chamber to said patient in response to said initial volume signal;
releasing exhalation gas from said closed loop while reducing the volume of said variable volume chamber during a first time period sufficient to substantially increase the enhanced gas concentration of said exhalation gas;
thereafter terminating release of said exhalation gas from said closed loop and recirculating gas within said closed loop while adding enhanced gas to said closed loop in response to said detected enhanced gas concentration and increasing the volume of said variable volume chamber.

22. The method as defined in claim 21 wherein the combination of said desired oxygen concentration and said desired enhanced gas concentration is greater than 40% by volume.

23. The method as defined in claim 21, wherein said selected initial volume is less than approximately 5 liters.

24. The method as defined in claim 21, wherein said enhanced gas in said closed loop is maintained at a concentration of greater than 10% by volume.

25. Apparatus for conducting enhanced gas inhalation of a patient, comprising:
an oxygen source;
an enhanced gas source;
a flexible bag defining a variable volume chamber for receiving said inhalation gas;
conduit means for series interconnecting said variable volume chamber and said patient in a closed loop;
a gas discharge port in fluid communication with said conduit means for releasing gas from said closed loop;
oxygen sampling means in fluid communication with said conduit means for detecting oxygen concentration within said closed loop;
enhanced gas sampling means in fluid communication with said conduit means for detecting enhanced gas concentration within said closed loop;
control means for providing preselected oxygen and enhanced gas concentration values;
oxygen input valve means in fluid communication with said conduit means for selectively inputting oxygen from said oxygen source to said closed loop in response to a detected oxygen concentration value from said oxygen sampling means less than said preselected oxygen concentration value from said control means;
enhanced gas input valve means in fluid communication with said conduit means for selectively inputting enhanced gas from said enhanced gas source to said closed loop in response to a detected enhanced gas concentration value from said enhanced gas sampling means less than said preselected enhance gas concentration value from said control means;
carbon dioxide removal means in fluid communication with said conduit means for removing carbon dioxide from said closed loop;
volume indicator means for detecting when said variable volume chamber obtains an initial volume of a selected value;
valve means responsive to the detection of said selected value by the volume indicator means for automatically opening to initiate fluid communication between said flexible bag and said patient.

26. The apparatus as defined in claim 25, further comprising:
a rigid housing defining a substantially fixed volume chamber for receiving said flexible bag; and
a gas pressure line for inputting pressurized gas to said rigid housing for compressing said flexible bag and expelling inhalation gas from said flexible bag to said patient.

27. The apparatus as defined in claim 25, further comprising:
an air sample/ventilator line for introducing gas having a desired oxygen concentration into said closed loop; and
pump means for circulating said inhalation gas within said closed loop.

28. The apparatus as defined in claim 25, wherein said indicator means comprises:
a light source for illuminating said flexible bag; and
a light detector for producing a signal indicative of said flexible bag obtaining said predetermined mimimum volume.

29. The apparatus as defined in claim 25, wherein said initial volume of a selected value is in the range of from 4 liters to 5 liters.

* * * * *